United States Patent [19]

Magnotta

[11] Patent Number: 4,581,266

[45] Date of Patent: Apr. 8, 1986

[54] HEAT TRANSFERABLE LAMINATE

[75] Inventor: Frank A. Magnotta, Framingham, Mass.

[73] Assignee: Dennison Manufacturing Company, Framingham, Mass.

[21] Appl. No.: 708,098

[22] Filed: Mar. 4, 1985

Related U.S. Application Data

[63] Continuation of Ser. No. 501,454, Jun. 6, 1983, abandoned.

[51] Int. Cl.$^{4}$ .................................. A61F 13/02

[52] U.S. Cl. .................................. 428/40; 428/187; 428/200; 428/352; 428/485; 428/486; 428/488.4; 525/277; 156/240

[58] Field of Search ................. 428/485, 486, 200, 40, 428/187, 484, 352; 525/277, 275, 487–489; 156/240, 230

[56] References Cited

U.S. PATENT DOCUMENTS 2,862,832 12/1958 Shepherd .......................... 428/200

2,990,311 6/1961 Shepherd .......................... 428/486

3,816,015 10/1971 kingston .......................... 428/485

3,944,695 3/1976 Kosaka et al. ...................... 117/3.2

*Primary Examiner*—Edith Buffalow

*Attorney, Agent, or Firm*—Barry D. Josephs

[57] ABSTRACT

An improved release coating for heat transferable laminates wherein an ink design layer is transferred from a carrier web onto an article such as a plastic or glass container upon application of heat and pressure. The improved release coating transfers with the ink design layer and forms an optically clear protective coating over the transferred ink design layer. The transferred release coating upon resolidification has an exceedingly high optical clarity, with no hazing, spotting, or halo discernible over the transferred ink design layer. The improved release coating incorporates a tackifying resin in a wax base. The wax base includes a montan wax and a crystalline wax such as paraffin wax. The wax base may also include a microcrystalline wax component. The preferred tackifying resin is selected from the polyterpene class.

9 Claims, 2 Drawing Figures

HEAT TRANSFERABLE LAMINATE

This application is a continuation of application Ser. No. 501,454, filed June 6, 1983, now abandoned.

BACKGROUND OF THE INVENTION

1. Field of the Invention

The present invention relates to a heat transferable label and improved release composition therefor.

2. Description of the Prior Art

Prior art heat transferable labels for imprinting designs onto an article typically involve decorative laminates consisting of a paper base sheet or web coated with a wax or polymeric release layer over which a design is imprinted in ink.

U.S. Pat. No. 3,616,015 is illustrative of the prior art. In U.S. Pat. No. 3,616,015 a label carrying web such as a paper sheet includes a heat transferable label composed of a wax release layer affixed to a surface of the paper sheet and an ink design layer superimposed onto the wax release layer. In the heat transfer labelling process for imprinting designs onto articles, the label carrying web is subjected to heat and the laminate is pressed onto an article with the ink design layer making direct contact with the article. As the web or paper sheet is subjected to heat, the wax layer begins to melt so that the paper sheet can be released from the wax layer. After transfer of the design to the article, the paper sheet is immediately removed, leaving the design firmly affixed to the surface with the wax layer exposed to the environment. The wax release layer should not only permit release of the transferable label from the web upon application of heat to the web but also form a clear protective layer over the transferred ink design.

This commonly assigned patent discloses a wax release coating containing a modified montan wax which has been oxidized, esterfied, and partially saponified. In order to attain improved clarity of the transferred ink design the transferred wax coating over the ink design is subjected to additional heat processing after the label has been transferred onto an article. The additional processing involves postflaming, wherein the transferred wax coating is subjected to jets of high temperature gas either as direct gas flame or as hot air jets at temperatures of about 300° F. to 400° F. for a period of time sufficient to remelt the wax coating without substantially heating the bottle. Upon cooling of the remelted wax coating through use of ambient or forced cooled air, the cooled wax layer solidifies to form a clear, smooth protective coating over the transferred ink design. Although the heat transferable label and process disclosed in U.S. Pat. No. 3,616,015 represents an improvement over prior heat transferable labels, they are best suited to decoration of plastic articles which are not transparent. Although the heat transferable label disclosed in this reference may be utilized for decorating a wide variety of different plastics, there can be a degree of hazing or halo noticeable over the transferred label when the transfer is made onto clear plastic materials, despite use of postflaming. U.S. Pat. No. 3,616,015 is herein incorporated by reference.

U.S. Pat. No. 2,990,311 discloses a heat transferable decal having a release transfer layer composed of a mixture of a crystalline wax and a synthetic thermoplastic film-forming resin, principally an organic linear thermoplastic film-forming resin which is substantially water insoluble. The degree of compatibility of the resin and wax is controlled through selection and ratio of the components to give heat transfers of either the hot peel or cold peel type. In the hot peel transfer, the decal will adhere and release from the backing only immediately after application while the decal is still hot. In the cold peel transfer the transferred decal will adhere to the receiving surface when hot but will only release and transfer by peeling away the backing after the transfer has cooled. In either type of transfer, this reference teaches that resins and waxes (the latter being used for the release layer) should be mutually incompatible or insoluble at temperatures below the melting temperature of the wax such that the molten wax, upon cooling, will actually crystallize separately and distinctly from the resin. The resins are linear thermoplastic film-forming resins defined as essentially solvent-soluble, softened by heat and to involve only a minor amount or no cross-linkage.

Suitable resins specifically disclosed are polyvinyl acetate, polyethyl acrylate, polymethyl acrylate, polyethyl methacrylate, polypropyl methacrylate, polybutyl methacrylate, styrenebutadiene, acrylonitrile-butadiene, polychloroprene rubbers, polyvinyl butyral, ethyl cellulose, and polyvinyl acetate vinyl stearate copolymer (col. 5, l. 38–44). The reference teaches that the wax component should be a material which derives its crystallinity mainly from the presence of long hydrocarbon chains and should melt over a relatively narrow range between the temperatures of about 50° C. to 110° C. The penetrometer hardness value (ASTM D5-52) when tested with 100 grams for 5 seconds at 28° C. should be below about 15. Specific waxes disclosed as suitable are beeswax, candelilla wax, carnauba wax, hydrogenated castor oil, montan wax, paraffin wax, low molecular weight polyethylene, oxidized microcrystalline wax, and hard wax or derivatives thereof obtained from the Fischer Tropsch synthesis. (col. 5, l. 45–56). This reference does not disclose applicant's formulation for the release layer nor does it contemplate the advantages which applicant has derived from such formulation. U.S. Pat. No. 2,990,311 is herein incorporated by reference.

U.S. Pat. No. 2,862,832 discloses a heat transferable decal having a release layer composed of an oxidized wax. The disclosure is directed principally to defining the type of wax found to provide suitable release of the decal from the carrier web upon application of heat. The wax disclosed in this reference is an oxidized wax obtained as the reaction product of the oxidation of hard, high melting, aliphatic, hydrocarbon waxes. The oxidized waxes are defined as the oxidation products of both natural and synthetic hydrocarbon waxes such as petroleum waxes, low molecular weight polyethylene and waxes obtained from the Fischer-Tropsch synthesis. Suitable wax may include oxidized microcrystalline wax or the esterification product of an oxidized hydrocarbon wax. The oxidized waxes are disclosed as those having melting points between about 50° C. and 110° C., saponification values between about 25 and 100, acid values between about 5 and 40, and penetrometer hardness (ASTM D5-52) below about 51 as measured with 100 grams for 5 seconds at 25° C.

Although this reference mentions that minor amounts of certain additives such as fillers and resins may be added to the oxidized wax, the invention is clearly concerned with the use of wax as the essential component and designation of specific wax types found to give advantageous results. This reference does not disclose applicant's principal additives or applicant's combined formulation nor does it recognize or contemplate the advantages obtained from such formulation. U.S. Pat. No. 2,862,832 is herein incorporated by reference.

U.S. Pat. No. 3,616,176 discloses a heat transfer laminate of a type related to that disclosed in U.S. Pat. No. 3,616,015. In U.S. Pat. No. 3,616,176 the laminate is composed of a base sheet, with a polyamide layer covering the base sheet and a decorative ink layer covering the polyamide layer. Sufficient heat is applied to the laminate to heat the polyamide layer at or above a softening point, and the laminate is then pressed onto the surface of an article with the decorative ink layer coming into direct contact. Upon withdrawal of the heat source, the polyamide layer cools to a temperature below the softening point and the base sheet is removed. The decorative layer becomes fused or heat sealed to the article. The polyamide layer in ths disclosure functions as a release coating which allows transfer of the decorative layer onto an article and upon cooling serves as a protective coating layer over the transferred decorative layer. The use of a polyamide release coating has the principal disadvantage in that there is a significant tendency for the polyamide to form a noticeable halo around the transferred decorative layer. Also the polyamide layer even when subjected to additional processing such as post-flaming does not form sufficiently clear coating that would esthetically permit heat transfer labelling onto clear articles or bottles.

U.S. patent application Ser. No. 130,303 file date Apr. 14, 1980, commonly assigned with the present application, discloses a heat transfer label of the type illustrated in U.S. Pat. No. 3,616,015. The heat transfer label disclosed in Ser. No. 130,303 is composed of a carrier member (base sheet) overcoated in designated regions with a release layer and an ink design layer. Optionally, a barrier layer is included between the release layer and the ink layer. The release layer is typically composed of a polymerization product of a diamine with the dimer of a fatty acid. In order to reduce the halo effect of the transferred release layer over the ink design layer, the release layer is contoured in a particular manner. To further reduce the halo effect, this reference teaches that the optional barrier layer included between the release layer and ink layer, be formed of an aromatic acid-based polyester covering and overlapping the release layer by a margin.

U.S. patent application Ser. No. 146,999 file date May 6, 1980 commonly assigned with the present patent application, also discloses a heat transfer label of the type illustrated in U.S. Pat. No. 3,616,015. The heat transfer label disclosed in Ser. No. 146,999 is composed of a carrier member (base sheet) overcoated in designated regions with a release wax layer, a protective barrier layer, an ink design layer, and an adhesive layer. The protective (barrier) layer is placed preferably between the release wax layer and the ink design layer. The protective layer provides enhanced chemical resistance for the heat transfer label and permits the heat transfer label to resist distortion during the heat transfer process without sacrifice in label clarity.

Accordingly, it is an object of the present invention to provide an improved release for heat transferable substrates which permits transfer of an ink design image from a support member to a plastic or glass container.

It is an important object to provide a release which has improved optical clarity and required release and adhesive properties.

It is a further object to provide an improved release and heat transferable substrate for use in transfer of optically clear design image from a support to a clear plastic or glass container. A related object is to provide an improved optically clear release which also functions as a protective coating for the transferred image.

SUMMARY OF THE INVENTION

In accomplishing the foregoing and related objects, the invention provides a heat transferable laminate having an improved release composition. The heat transferable laminate of the invention is typically affixed to a carrier web such as a paper or plastic sheet. The transferable laminate is composed of a release layer coated on the carrier web, an ink design layer, and an optional adhesive coating over the ink design layer. As heat and pressure is applied to the laminate in contact with an article such as a glass or plastic container, the release layer softens allowing the laminate which contains the decorative ink design to transfer onto the article to be decorated. The release coating remains with the laminate, forming an optically clear, glossy, protective coating over the transferred ink design layer after the release coating resolidifies. The transferred laminate may be subjected to postflaming to improve the smoothness and gloss of the transferred release coating which forms the protective coating.

An important aspect of the invention is an improved formulation for the release layer. The improved release formulation has the advantage that it produces an optically clear, transparent, protective layer over the transferred ink design layer. Consequently, the improved release coating has distinct advantage in the application of heat transferable laminates to plastic or glass containers, and in particular to clear plastic or glass containers.

The clarity of the transferred release coating forming a protective coating over the transferred ink design layer is of a degree heretofore unachievable. The transferred release layer is optically clear to the unaided eye when viewed against a clear plastic or glass container. There is no hazing, spotting, or halo effect discernible over the transferred ink design layer regardless of whether the heat transferable laminate is applied to opaque or clear articles.

The improved release layer of the invention contains a crystalline wax such as paraffin wax or microcrystalline wax, and a tackifying agent. Preferably the improved release contains a crystalline wax, such as paraffin wax, a montan wax, and tackifying resin. It has been determined to be highly desirable to select a tackifying resin which is composed of an optically clear, nonwax hydrocarbon polymer having a softening point (Ball and Ring method) between about 80° C. and 135° C., and a color Gardner number of about 4 or less, more preferably between about 1 and 3. The preferred tackifying resin improves the adhesiveness of the release layer without destroying the release properties of the wax. The tackifying resin also enhances the optical clarity of the release layer. The polyterpene class in general has been determined to be most advantageous. One preferred polyterpene tackifying resin contains piperylene and isoprene units. Another preferred polyterpene tackifying resin consists principally of beta-pinene and dipentene. The paraffin wax is composed of linear, saturated hydrocarbons ranging from $C_{26}H_{54}$ to $C_{32}H_{66}$ having a melting range between about 145° F. to about 155° F. The preferred montan wax is an oxidized, esterified, partially saponified montan wax.

Applicant has determined that inclusion of a tackifying resin from the polyterpene class increases the adhesiveness of the release layer without destroying the release properties of the wax and simultaneously, quite unexpectedly, reduces the amount of crystalline structure of the solidified wax to a greater degree than might be expected from dilution of the wax with other resins or diluents in the same proportion. The significant reduction in total crystallinity of the wax is believed to markedly enhance the optical clarity of the wax upon resolidification.

A preferred formulation for the improved release coating may also include microcrystalline wax. The microcrystalline wax is typically composed of saturated hydrocarbons of higher melting point than that of paraffin wax. The microcrystalline wax is characteristically composed of about $C_{34}H_{70}$ to $C_{60}H_{120}$ hydrocarbons.

In addition to the microcrystalline wax, the preferred formulation for the improved release coating may advantageously contain a resin binder, which binds the components of the release in a homogeneous mixture which forms a hot melt and thus obviates the need for a solvent. A preferred binder is a copolymer of ethylene and vinylacetate or a terpolymer of ethylene, vinyl acetate and acrylic acid.

In the preferred release formulation, the paraffin wax may be present in an amount between about 15 to 30 weight percent; the montan wax between about 15 to 35 weight percent; and the tackifying resin in an amount between about 15 to 50 weight percent. The weight ratio of montan wax to tackifying resin advantageously falls in the range from about 0.3/1 to 2.3/1. The improved release formulation of the invention is applicable to any heat transferable laminate of the type wherein the objective is to transfer an ink design image from a carrier web to an article upon the application of heat and pressure to the laminate.

DETAILED DESCRIPTION

Figure 1:
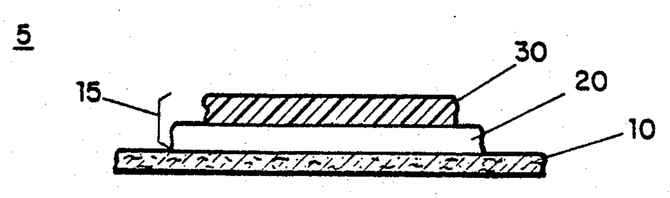
FIG. 1 is an illustration of a preferred embodiment of the composite heat transferable laminate.
Figure 2:
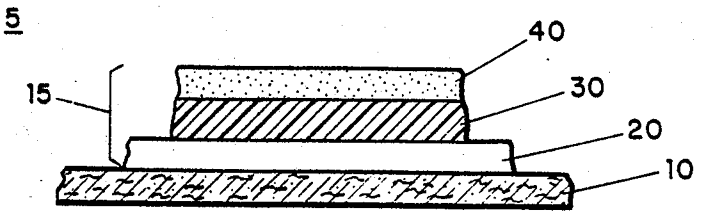
FIG. 2 is an illustration of another preferred embodiment of the composite heat transferable laminate.

The preferred embodiment of the heat transferable laminate 5 of the invention as illustrated in FIG. 1 is composed of a carrier web 10, typically paper, overcoated with a release layer 20 and ink design layer 30. Optionally an adhesive layer 40 may be included over design layer 30 as illustrated in FIG. 2. Release layer 20, design layer 30 and optional adhesive layer 40 form a transferable substrate 15, which releases from carrier web 10 upon application of heat to web 10 sufficient to melt release layer 20. As an article or surface is pressed onto the exposed surface of substrate 15, it splits from carrier web 10 and transfers onto the surface of the article with ink design layer 30 clearly imprinted on the article.

The heat transferable laminate of the invention satisfies a number of requirements simultaneously. Release layer 20 and ink design layer 30 are first of all easily coated onto carrier web 10 when the release layer is in a molten state. Coating of carrier 10 is readily effected preferably by gravure methods but other printing methods such as letterpress, flexographic, or screen printing as well as cast coating methods such as reverse roller coating may be employed in coating release layer 20 onto carrier web 10. Ink design layer 30 is readily coatable on release layer 20 by use preferably of gravure technique, although other cast coating methods and screen printing methods may also be used. Release layer 20 and ink design layer 30 of the invention have the required physical properties that permit coating by the preferred gravure technique without "pick off" problems occurring; that is, without causing removal of a portion of release layer 20 as the ink design layer 30 is coated thereon. Release layer 20 also has the required properties that prevent embossing of the wax during printing of design layer 30 and also prevents ink striking into the wax during printing and ink migration into the wax after printing. Release layer 20 is of a formulation which also prevents nonuniform splitting of the release layer during the heat transfer process and thereby prevents insufficient or uneven transfer of the release layer from the carrier web during the transfer process. In addition to having the requisite release property upon heating, release layer 20 also has sufficient adhesive properties upon cooling which keeps design layer 30 adhesively bonded to the article being imprinted and also forms a clear glossy protective coating layer over the transferred design layer 30. The clarity, smoothness, and glossiness of release layer 20 is improved by subjecting transfer substrate 15 to postflaming after substrate 15 has been transferred to an article. The postflaming may be accomplished by exposing the transferred substrate to jets of hot gas either as direct gas flame or as hot air jets for a period of time sufficient to remelt the wax, as for example by the methods described in U.S. Pat. No. 3,616,015, herein incorporated by reference. After postflaming layer 20 resolidifies quickly upon exposure to ambient conditions to form a smooth, glossy film of improved clarity. The resolidified layer exhibits so high a degree of clarity and translucency that there is virtually no visible halo or hazing either around or over the surface of the transferred design image 30. This results in remarkable clarity in the transferred design image. Thus, the laminate 5 is suitably applied to plastic and glass articles of a variety of shades, as well as to articles and containers composed of optically clear plastic materials such as polyvinylchloride and polyethylene terephthalate or clear polyethylene or polypropylene. Prior art heat transferable laminates, although exhibiting high degree of optical clarity upon postflaming, have some limitation in application to optically clear plastics since there can be some hazing or halo discernible upon transfer onto optically clear materials.

The virtual elimination of hazing or halo has been accomplished while simultaneously satisfying all other physical property requirements for an effective release coating for a heat transferable substrate as has been discussed in the foregoing. Additionally this improvement has been made while reducing the amount of montan wax in the preferred formulation. Since montan wax is a costly constituent, applicant has realized significant cost savings in the preferred formulation for release coating 20.

The preferred formulation for release layer 20 is a hot melt containing paraffin and a montan wax which may also include a minor amount of microcrystalline wax. In addition to these waxes, the formulation includes a tackifying resin and suitable binder. Applicant has discovered quite unexpectedly that, with proper selection of tackifier resin, the total amount of crystallinity of the paraffin wax can be reduced significantly, more than would occur by addition of other resins or diluents of equal amount. It is not known with certainty all of the factors responsible for the high degree of clarity and translucency of the transferred layer 20, but the reduction in inherent crystalline structure of the paraffin wax and to an extent the microcrystalline wax, as well, is believed to be the principal factor. Although it is known that the inherent crystallinity of certain waxes, particularly paraffin wax, used in release coating for heat transferable laminates is a principal cause of the hazing effect, it has been heretofore not been possible to reduce the crystallinity of the solidified wax without disrupting other important physical properties of the release layer. Although postflaming serves to reduce some of the hazing which appears over the transferred image it effects only a partial reduction and does not decrease the crystallinity of the wax components. Postflaming has been determined to increase clarity principally because it has the effect of smoothing microscopic hills and valleys on the surface of the transferred release layer. Postflaming thus creates a smoother, more uniform surface of glossy character, increases the overall clarity of the transferred release layer, and consequently the clarity of the transferred design image. Residual amount of opacity or hazing is believed to be caused by the crystalline structure of the solidified paraffin wax and to a lesser degree of the solidified microcrystalline wax which contains crystals of much smaller size.

It is desirable to select a thermoplastic tackifying resin which is composed of an optically clear, nonwax hydrocarbon polymer having a softening point (Ball & Ring Method ASTM E-28) between about 80° C. and 135° C., more preferably between about 100° C. and 125° C. Applicant has found a particular polymer class, the polyterpenes, which when added to the release formulation, increases the adhesiveness of the release layer and quite unexpectedly reduces the amount of crystalline structure in the solidified wax. This reduction is greater than might be expected from dilution of the wax with other resins or diluents added in the same proportion. The marked reduction in total crystallinity of the wax, it is theorized, enhances the optical clarity of the wax upon resolidification. The solidified release layer has a color Gardner No. between about 1 and 4. The tackifying resin also preferably has a color Gardner number between about 1 and 4.

The polyterpene class for the purposes of the present disclosure shall be construed broadly to include any polymer of terpene or any copolymer wherein at least one of the monomers is a terpene hydrocarbon. The terpene class shall include all hydrocarbons based on the isoprene unit $C_5H_8$ and having the general formula $(C_5H_8)_n$ (isoprenoid compounds) and may be either acyclic or cyclic with one or more benzenoid groups.

A preferred tackifying resin of the polyterpene class, which increases adhesiveness while markedly reducing the wax crystalline structure, contains piperylene (1,3 pentadiene) and isoprene polymer units. Illustrative polyterpene resins of this type include the Wingtack Series of polyterpene resins, particularly Wingtack-95, available from Goodyear Tire and Rubber Company, Chemical Division, Akron, Ohio. Specifically, Wingtack-95 polyterpene resin is a polymeric terpene containing principally piperylene and isoprene units with the remainder of the units comprised of mono-olefins. The ratio of piperylene to isoprene derived structures is at least about 8 or 9 to 1. Wingtack-95 has a ball and ring softening point of about 95° to 100° C., a color Gardner number typically about 3 or less, and an average molecular weight of about 1100. Further description of the Wingtack resins may be found, for example, in U.S. Pat. No. 4,028,292 herein incorporated by reference. Another preferred polyterpene tackifying resin having the above-described desirable effect is composed principally of beta-pinene and dipentene. A preferred resin of this type is the ZONAREZ or ZONATAC series of polyterpene resins, particularly ZONAREZ 7000 series which is available from Arizona Chemical Company of Wayne, N.J. The ZONAREZ 7000 series of polyterpene resins has a color Gardner number of about 3 or less. The preferred polyterpene resins in the ZONAREZ 7000 series have a ball and ring softening point between about 85° C. to 125° C., preferably between about 100° C. to 125° C. The use of a polyterpene tackifying resin in applicant's hot melt formulation for wax release layer 20 has an additional advantage over conventional resins such as pentarerythritol ester of hydrogenated rosin used in prior art wax release formulations. Such resins may oxidize over a period of time causing a dulling effect in the appearance of the transferred design image. In contrast, polyterpene based tackifying resins do not oxidize with time after the substrate 15 has been transferred onto an article.

The paraffin wax component of the formulation for release layer 20 is used to give layer 20 its principal release characteristic upon melting. Paraffin wax, a petroleum derived product, typically has a molecular weight between about 254 to 450 and is composed essentially of linear saturated hydrocarbons ranging from $C_{18}H_{38}$ to $C_{32}H_{66}$. Paraffins typically have a melting point from about 110° to 150° F. ("Melting point" as used herein refers to drop melting point). A preferred paraffin wax for use in the formulation of the present invention is composed of linear saturated hydrocarbons ranging from $C_{26}H_{54}$ to $C_{32}H_{66}$ having a melting point between about 145° F. to about 155° F.

The paraffin wax, a linear saturated hydrocarbon, is charcterized in that it crystallizes in both plate and needle-type crystals, particularly the former. Another type of crystalline structure, termed malcrystalline, is neither plate nor needle-like and is observable in the paraffin crystal structure in amount depending on the boiling point of the paraffin fraction being investigated. In paraffin wax fractions of lower boiling point, for example about 180° F. at 10 mm pressure, the entire crystalline structure is composed of plates. In paraffin wax fractions having somewhat higher boiling points, a minor amount of malcrystalline and needle-like structures may be observable interspersed among the plate-like structures. In general, the plate crystals predominate in paraffin waxes of any boiling range. However, in the higher melting paraffin waxes where there is likely to be some increased amount of branching associated with their structure, there is likely to be a greater portion of malcrystalline and needle-like crystals interspersed among the plates. The type and amount of crystals found in paraffin wax is principally an inherent function of the boiling point range of paraffins being investigated irrespective of the solvent or medium used from which the crystalline solid is precipitated.

Paraffin wax suitable for use in release layer 20 is sold in various grades which differ chiefly in melting point. Commercial grades of paraffin wax which may be used in release layer 20 are commonly designated as refined, semirefined, and crude grade waxes. Of these the refined grade is preferred for use in the present formulation for release layer 20. Paraffin wax of refined grade is obtainable from a number of sources, one of which is the Petrolite Corp., Bareco Division, of Tulsa, Okla.

The microcrystalline component of formulation 20 is composed of saturated hydrocarbons of higher melting point than those of paraffin wax. Microcrystalline waxes characteristically contain between about $C_{34}H_{70}$ to $C_{60}H_{120}$ hydrocarbons having molecular weight between about 478 and 840. Microcrystalline waxes (micro-waxes) are characterized by an increased amount of branching; although they contain straight chain molecules, they are not as linear a saturated hydrocarbon as paraffin wax. Also compared to paraffin wax, they contain a greater portion of cyclic ring molecules. The crystalline structure of the microcrystalline wax contains predominantly malcrystalline and needle-like crystals having very small undefined form when compared with the plate-like crystalline structure of paraffin wax under the same magnification. Thus the crystalline structure of microcrystalline wax is small and irregular when solidified from the melted wax. In solvents microcrystalline wax discloses no well-formed crystals of any size. Small amounts of microwax are advantageously added to the formulation for release layer 20, since microwax imparts a measure of plasticity to the paraffin wax components, since the paraffin wax is rather brittle and would by itself tend to cause cracks or fissures in a wax release layer. Because of its diminished crystalline structure, microwax contributes little potential hazing or halo effect.

The classes of microwaxes vary principally in their melting point range. For example, the so-called hard microwaxes have a melting point between about 190° to 210° F.; the plastic microwaxes a melting point between about 145° to 175° F.; the emulsifiable crystalline waxes between about 190° to 225° F.; and modified microwaxes between about 165° to 220° F. All of these various types of microwaxes may be employed in the present formulation; however, the plastic type (BARECO designation) is most preferred. An illustrative, commercially available microcrystalline wax which is particularly suitable in the present formulation is available under the Victory White tradename from the Petrolite Corp.

The montan wax component for release layer 20 is a coal (lignite) derived wax characterized by high concentration of montanic acid ($C_{28}H_{56}O_2$). Montan wax has been determined to be a very suitable additive to increase the hardness of release coating 20, as well as its lubricity. Additionally, montan wax promotes a smooth glossy texture of the release coating after transfer. Montan wax also prevents penetration of the release coating into the paper carrier 10, as its forms a formation of a hard protective barrier coating over the transferred design layer.

A particularly suitable type of montan wax is an oxidized, esterified, partially saponified montan wax as disclosed in U.S. Pat. No. 3,616,015, herein incorporated by reference. Montan waxes of this type have melting points (drop points) typically between about 50° and 110° C., saponification values between about 25 and 150, acid values between about 5 and 40, and penetrometer hardness (ASTM-D5-52) below about 15 as measured with 100 grams for 5 seconds at 25° C. These montan waxes also have relatively high melt viscosity. An illustrative oxidized, esterified, partially saponified montan wax is available under the tradename Hoechst OP or Hoechst X55 modified montan wax from the Hoechst Chemical Company, (location). Hoechst OP modified montan wax has a drop point (ASTM D127) of 212° to 221° F., a congealing point (ASTM D938-49) between 165° and 175° F., an acid number of 10 to 15, and a saponification number of 100 to 115. Hoechst X55 has a drop point of 208° to 218° F., a congealing point of 167° to 176° F., an acid number of 10 to 15, and a saponification number of 90 to 110. These waxes have melt viscosities of at least about 150 centipoise at a temperature of about 25° F. above their solidification point.

A particularly suitable binder in the preferred release formulation is a copolymer of ethylene and vinylacetate, such as that available under the tradename Elvax 410 from E. I. duPont Company, Wilmington, DE. The binder is used principally to bind the components of the release formulation (release layer 20) in a homogeneous mixture, which forms a hot melt and does not require a solvent. The various components of the release formulation do not copolymerize in any measure during the coating stage or during melting and subsequent resolidification of release layer 20. A binder of copolymer of ethylene and vinylacetate such as Elvax 410 is most preferred because it provides high optimum gloss in blends with wax. However, other binders of ethylene and vinylacetate copolymer, as for example, Elvax 210, 310, may be used. An alternative binder in the ELVAX series such as Elvax 4310 which is ethylene vinylacetate acrylic acid terpolymer has also been determined to be suitable. Also in place of the above-referenced binders acrylic acid terpolymer has also been determined to be an ethylene acrylic acid copolymer binder may be employed. A suitable binder of this latter type is available under the tradename AC-540 from Allied Chemical Company.

Preferred compositions for release layer 20 are shown in Table I. Although specific formulations for the release layer 20 are given in Table I, it has been determined that the paraffin wax may be present in release layer 20 in an amount between about 15 to 30 weight percent, preferably between about 20 to 25 weight percent. The montan wax may be present in release layer 20 in an amount between about 15 to 35 weight percent, and the tackifying resin in an amount between about 15 to 50 weight percent, preferably about 35 to 45 weight percent. The weight ratio of montan wax to tackifying resin may be in a range between about 0.3/1 to 2.3/1.

TABLE I

| FORMULATION | A Wt. % | B Wt. % | C Wt. % | D Wt. % | E Wt. % | F Wt. % |
|---|---|---|---|---|---|---|
| Paraffin Wax | 22 | 22 | 22 | 22 | 22 | 22 |
| Microcrystalline Wax: | 4 | 4 | 4 | 4 | 4 | 4 |
| (eg. BARECO Victory White) | | | | | | |
| Montan Wax: | 27 | 27 | 34 | 34 | 27 | 27 |
| (eg. Hoechst OP or X-55) | | | | | | |
| Tackifier Resin: | 41 | 41 | 34 | 34 | | |
| (Polyterpene- eg. WINGTACK-95) | | | | | | |
| (Polyterpene- eg. ZONAREZ-7115) | | | | | 41 | 41 |
| Binder: | 6 | | 6 | | 6 | |
| (Ethylene and Vinylacetate copolymer) ELVAX-410 | | | | | | |
| ELVAX-4310 | | 6 | | 6 | | 6 |

TABLE I-continued

| FORMULATION | A Wt. % | B Wt. % | C Wt. % | D Wt. % | E Wt. % | F Wt. % |
|---|---|---|---|---|---|---|
| TOTAL | 100 | 100 | 100 | 100 | 100 | 100 |

Any of the formulations of Table I can be prepared by adding the listed components in the proportions shown to a suitable heating vessel and stirred therein at a temperature of about 250° to 280° F. until a homogeneous hot melt mixture is obtained.

The hot melt is coated preferably by roller or gravure onto carrier 10 in any desired size and pattern, thus forming release layer 20. When coating with the preferred gravure technique, the thickness is conveniently adjusted by use of proper gravure cylinders. The thickness of coated release layer 20 is preferably less than about 0.001 inch. Other coating techniques such as cast coating, particularly reverse roller coating, letterpress, and flexographic techniques, may be employed.

After coating release layer 20 onto carrier 10, the coating quickly becomes solidified upon exposure to a water cooled roller. Upon solidification of release layer 20, an ink design layer 30 may be applied over this layer typically using the same coating technique previously employed.

The ink design layer 30 is preferably applied so that release layer 20 extends beyond the design layer. The ink design layer 30 may be composed of any conventional ink of any color. The ink may typically include resinous binder bases compatible with the ink pigment employed. The ink binder may be selected from a wide variety of conventional resinous bases such as polyamide, polyvinyl chloride, acrylics, and polyamide nitrocellulose.

It is advantageous to overlay ink layer 30 with an adhesive coating 40 which facilitates transfer of substrate 15 to the article to be decorated. In this case substrate 15 may therefore typically be composed of release layer 20, ink design layer 30 and adhesive layer 40 as illustrated in FIG. 2. Adhesive layer 40 may suitably be composed of a thermoplastic polyamide adhesive. A preferred thermoplastic polyamide adhesive is the reaction product of a diamine with a dimerized fatty acid such as that available under the tradename VERSAMID 900 series from Henkel Corp. of Minneapolis, Minn. It has been found advantageous to combine this polyamide constituent with a nitrocellulose base in adhesive layer 40.

In use, carrier web 10 is heated to a temperature typically from about 375° to 400° F., i.e. sufficient to melt the release coating 20. This may be conveniently accomplished by conveying laminate 5 over a hot platen for a period sufficient to melt release coating 20. Alternatively the article to which laminate 5 is to be applied may be preheated to a temperature sufficiently high to melt release layer 20 as laminate 5 is pressed against the article.

Laminate 5 is applied to the article to be decorated by pressing the heated laminate onto the article so that the topmost layer of transfer substrate 15, for example ink design layer 30 or optional layer 40 contacts the article. Rolling pressure is applied over the exposed surface of carrier 10 to effect transfer of substrate 15 onto the article. Thereupon carrier 10 is peeled from substrate 15 while release layer 20 is in molten state, leaving substrate 15 permanently affixed to the article with design image clearly visible through transferred release layer 20. Upon exposure to ambient conditions for a short period, release coating 20 solidifies to a clear, smooth glossy protective layer over transferred ink design image 30.

The clarity of the coating 20 over design image 30 at this point in the process is distinctly greater than the clarity of the transferred release layer at the same point in the process as described in U.S. Pat. No. 3,616,015. Transferred substrate 15 may optionally be exposed to postflaming to remelt transferred coating 20 and thus further improve the clarity and gloss of transferred coating 20 and consequently clarity of transferred design image 30. Postflaming may be accomplished, for example, by exposing the transferred substrate 15 including transferred coating 20 to jets of hot gas either as direct gas flame or as hot air jets typically at about 300° F. to 400° F. or higher for a period sufficient to melt the wax in the manner described in U.S. Pat. No. 3,616,015. Upon exposure to ambient atmosphere coating 20 resolidifies to a film of such high degree of clarity and transparency that hazing or halo effects are virtually undetectable by the unaided eye. The clarity of transferred coating 20 and design image 30 is such that the heat transferable substrate herein described may be used to decorate virtually any plastic or glass article. For example, the substrate 15 is well suited to the decoration of such materials as polyvinyl chloride, polethylene terephthalate, polyethylene, and polypropylene.

Although the invention has been described within the context of particular embodiments for the transferable substrate, the invention is not intended to be limited to any particular composition or layer structure for the transferable substrate. It is known that the transferable substrate may contain other coating layers, for example, a plurality of ink design layers or separate adhesive layer over the ink design layer as well as barrier type layers between the ink design layer and release layer. The invention is equally applicable to such varying heat transferable structures. It should be appreciated that the release formulation of the invention has wide application as a release coating for any heat transferable substrate in contact with a support member such as a carrier web. The invention, therefore, is not intended to be limited to the description in the specification but rather is defined by the claims and equivalents thereof.

I claim:

1. An improved heat transferable laminate of the type comprising a substrate affixed to a support member for transfer from the support member to an article upon application of heat to the support member while said article contacts the substrate, wherein the substrate comprises in sequence a release layer in contact with the support member and an ink design layer over the release layer, wherein an improved release layer comprises:

a paraffin wax comprising linear saturated $C_{18}$ to $C_{32}$ hydrocarbon having a melting point between about 110° F. and 150° F., a montan wax being oxidized, esterified, and partially saponified, and a thermoplastic tackifying resin comprising a transparent nonwax hydrocarbon polymer comprising polyterpene, said tackifying polymer having a softening point between about 80° C. and 135° C., which tackifying polymer resists oxidation under ambient conditions and has a Color Gardner No. of between about 1 and 4, the tackifying polymer's resistance to oxidation preventing dulling of the ink design layer after the substrate has been transferred to an article, wherein the paraffin wax comprises between about 15 to 30 percent by weight of said release layer, the montan wax comprises between about 15 to 35 percent by weight of said release layer and the tackifying polymer comprises between about 15 to 50 percent by weight of said release layer.

2. A heat transferable laminate as in claim 1 wherein the wax component further comprises a microcrystalline wax.

3. A heat transferable laminate as in claim 1 wherein the tackifying resin is formed by the polymerization of isoprene and piperylene.

4. A heat transferable laminate as in claim 1 wherein the tackifying resin is formed by the polymerization of beta-pinene and dipentene.

5. A heat transferable laminte as in claim 1 wherein the release layer further comprises a resin binder selected from the group consisting of ethylene-vinyl acetate copolymer and ethylene vinyl acetate acrylic acid terpolymer.

6. A heat transferable laminate as in claim 2 wherein the microcrystalline wax comprises saturated $C_{34}$ to $C_{60}$ hydrocarbons having a melting point between about 145° to 175° F.

7. A heat transferable laminate as in claim 1 wherein the release layer in solid state has a color Gardner No. of between about 1 and 4.

8. A heat transferable laminate as in claim 6 wherein the weight ratio of montan wax to tackifying resin is in a range between about 0.3/1 to 2.3/1.

9. An improved heat transferable laminate of the type comprising a substrate affixed to a support member for transfer from the support member to an article, wherein the substrate comprises in sequence a release layer and ink design layer, said release layer in contact with the support member, the improvement comprising:

the release layer comprising a paraffin wax, an oxidized esterified, partially saponified montan wax and a thermoplastic tackifying polymer comprising a transparent non-wax hydrocarbon polymer comprising polyterpene, said tackifying polymer having a softening point between about 80° C. and 135° C. which tackifying polymer resists oxidation under ambient conditions and has a color Gardner No. of between about 1 and 4, the tackifying polymer's resistance to oxidation preventing dulling of the ink design layer after the substrate has been transferred to an article.

* * * * *